(12) United States Patent
Kuse et al.

(10) Patent No.: US 11,898,275 B2
(45) Date of Patent: Feb. 13, 2024

(54) CARBON FIBERS WHICH CAN BE PRODUCED REGENERATIVELY OR PART-REGENERATIVELY FROM CO2 USING COMBINED PRODUCTION METHODS

(71) Applicants: Kolja Kuse, Munich (DE); Uwe Arnold, Potsdam (DE); Thomas Brück, Moosinning (DE)

(72) Inventors: Kolja Kuse, Munich (DE); Uwe Arnold, Potsdam (DE); Thomas Brück, Moosinning (DE)

( * ) Notice: Subject to any disclaimer, the term of this patent is extended or adjusted under 35 U.S.C. 154(b) by 0 days.

(21) Appl. No.: 17/487,503

(22) Filed: Sep. 28, 2021

(65) Prior Publication Data
US 2022/0081806 A1  Mar. 17, 2022

Related U.S. Application Data

(63) Continuation of application No. 16/346,638, filed as application No. PCT/EP2017/001269 on Oct. 30, 2017, now abandoned.

(30) Foreign Application Priority Data

Nov. 1, 2016  (DE) .................... 20 2016 006 700.2

(51) Int. Cl.
*D01F 9/22* (2006.01)
*C08F 220/44* (2006.01)
*C08F 120/44* (2006.01)
*C12P 7/6445* (2022.01)

(52) U.S. Cl.
CPC .............. *D01F 9/22* (2013.01); *C08F 120/44* (2013.01); *C08F 220/44* (2013.01); *C12P 7/6445* (2013.01)

(58) Field of Classification Search
CPC ................................ D01F 9/22; C08F 220/44
See application file for complete search history.

(56) References Cited

U.S. PATENT DOCUMENTS

2010/0047153 A1 * 2/2010 Plee .......................... D01F 9/22
423/447.2

FOREIGN PATENT DOCUMENTS

WO  WO-2016113140 A1 * 7/2016 .............. D01F 9/22

OTHER PUBLICATIONS

Milbrandt et al., "Carbon Fiber From Biomass" date: Sep. 23, 2016 website: www.nrel.gov/docs/fyl 16osti/66386 (Year: 2016).*

* cited by examiner

*Primary Examiner* — Robert D Harlan
(74) *Attorney, Agent, or Firm* — Mark M. Friedman

(57) ABSTRACT

The invention describes carbon fibers which are produced on the basis of different process chains from CO2. These include routes through natural resources such as algal biomass to produce carbon fiber precursors such as PAN from CO2, as well as the purely synthetic route via the Fischer-Tropsch synthesis, which is also used to make CO2 carbon fiber precursors. In this way, CO2 from anthropogenic origin is to be converted into a solid aggregate state of carbon fiber, which can be disposed of at the end of its life cycle, after being used as highly valuable building material for industry and man, for the construction of buildings and vehicles. These processes produce by-products such as biodiesel and nutrients that generate added value. The production volumes of the resulting substances should be controllable by combining the methods presented here. Some of these processes alone have no long-term climate relevance because of the high costs, but in the initial phase of such a development with the help of carbon dioxide certificates or socio-political necessities they are able to quickly show that carbon fiber building materials can be produced which by themselves are made from CO2 and at least have the quality to be used in the construction sector and for example are feasible to replace steel, in that the paradigm of todays material production being CO2-positive, can be turned into the opposite. If the processes—which have the disadvantage of large-area consumption on the one hand and the of the lack of energy efficiency in the longer term on the other—can be coupled, they have the potential to support each other. By combining the methods, land use and costs can be adjusted to current regional economic performance based on the material paradigm of the future of carbon-negative production of carbon fibers, also depending on the current evolution of CO2 emission allowance prices. The invention has the desired effect in climate policy that high-tech technology transfer can take place into the currently disadvantaged regions of the world, which promotes the economic performance of today's disadvantaged regions and in particular creates the urgently needed jobs in these regions.

4 Claims, 9 Drawing Sheets

Fig. 9

Figure 1:
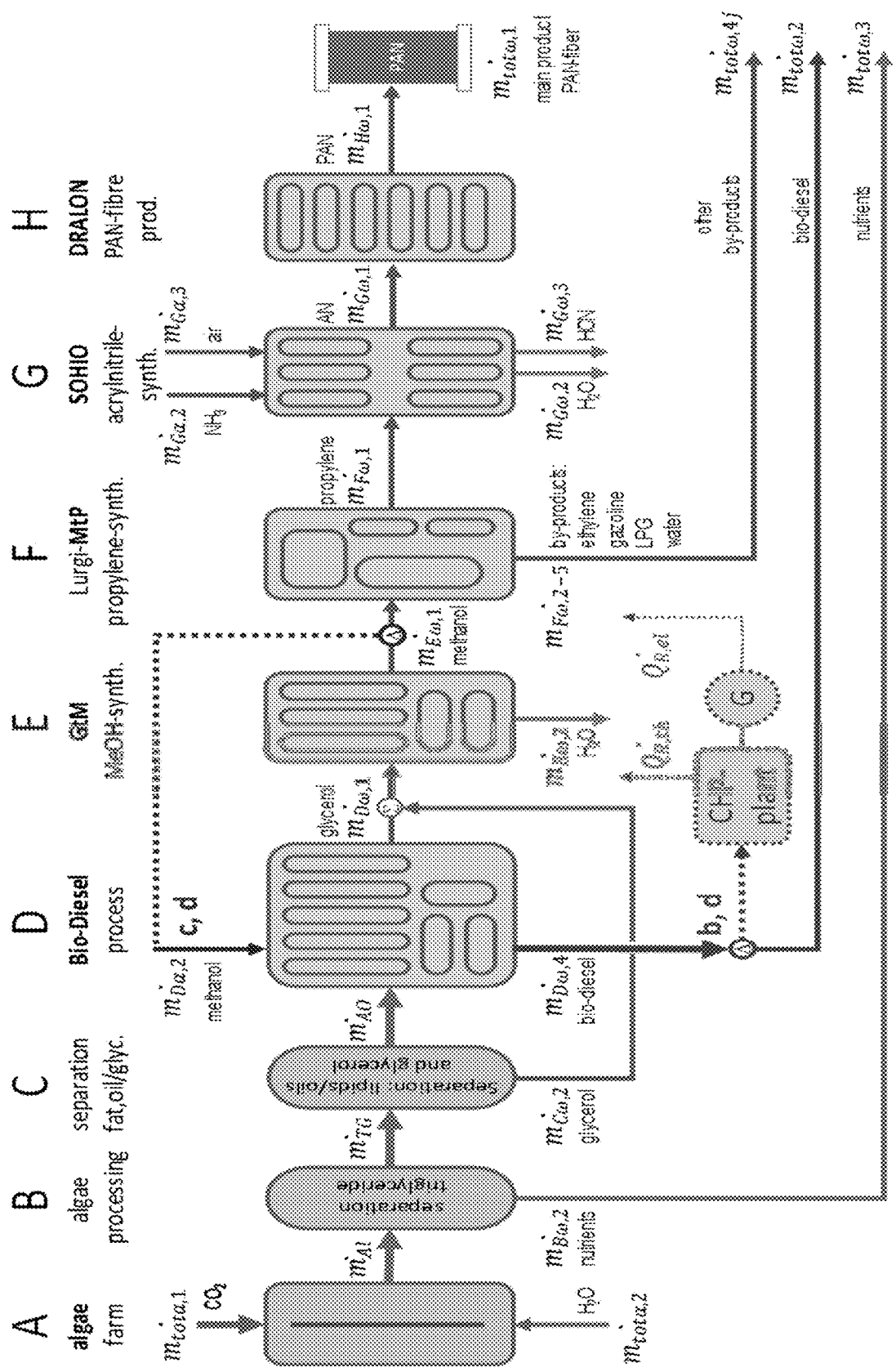
Figure 2:
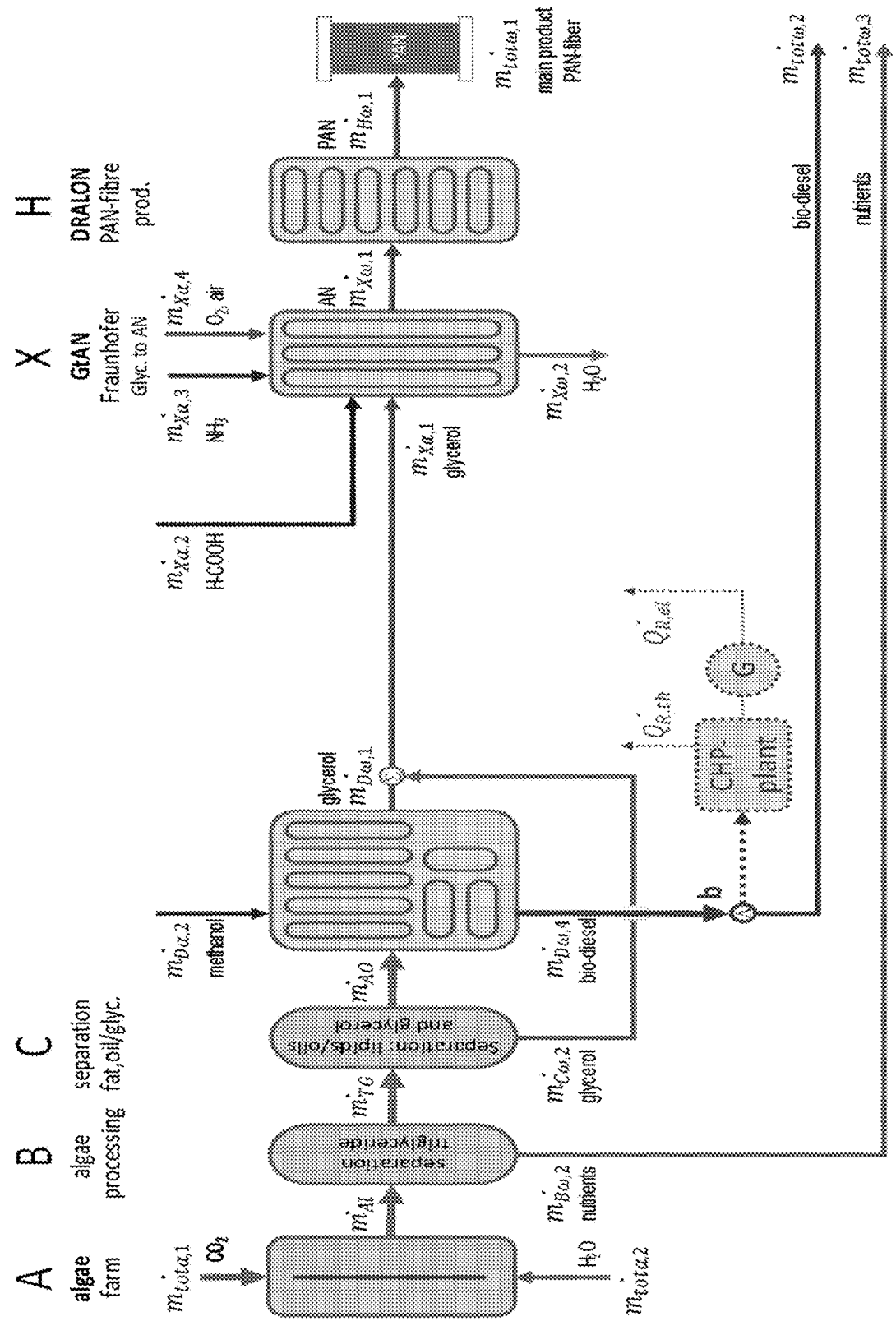
Figure 3:
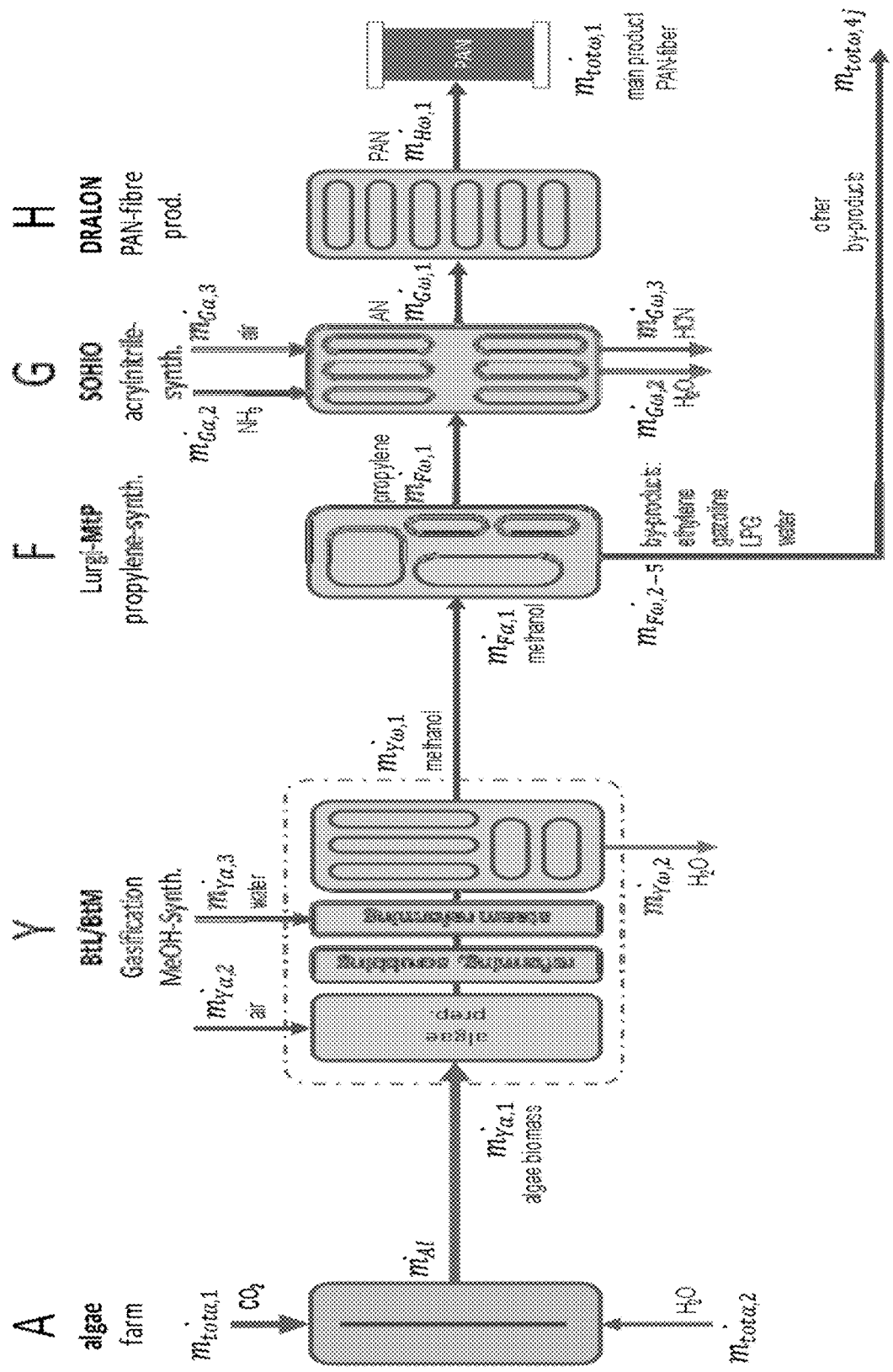
Figure 4:
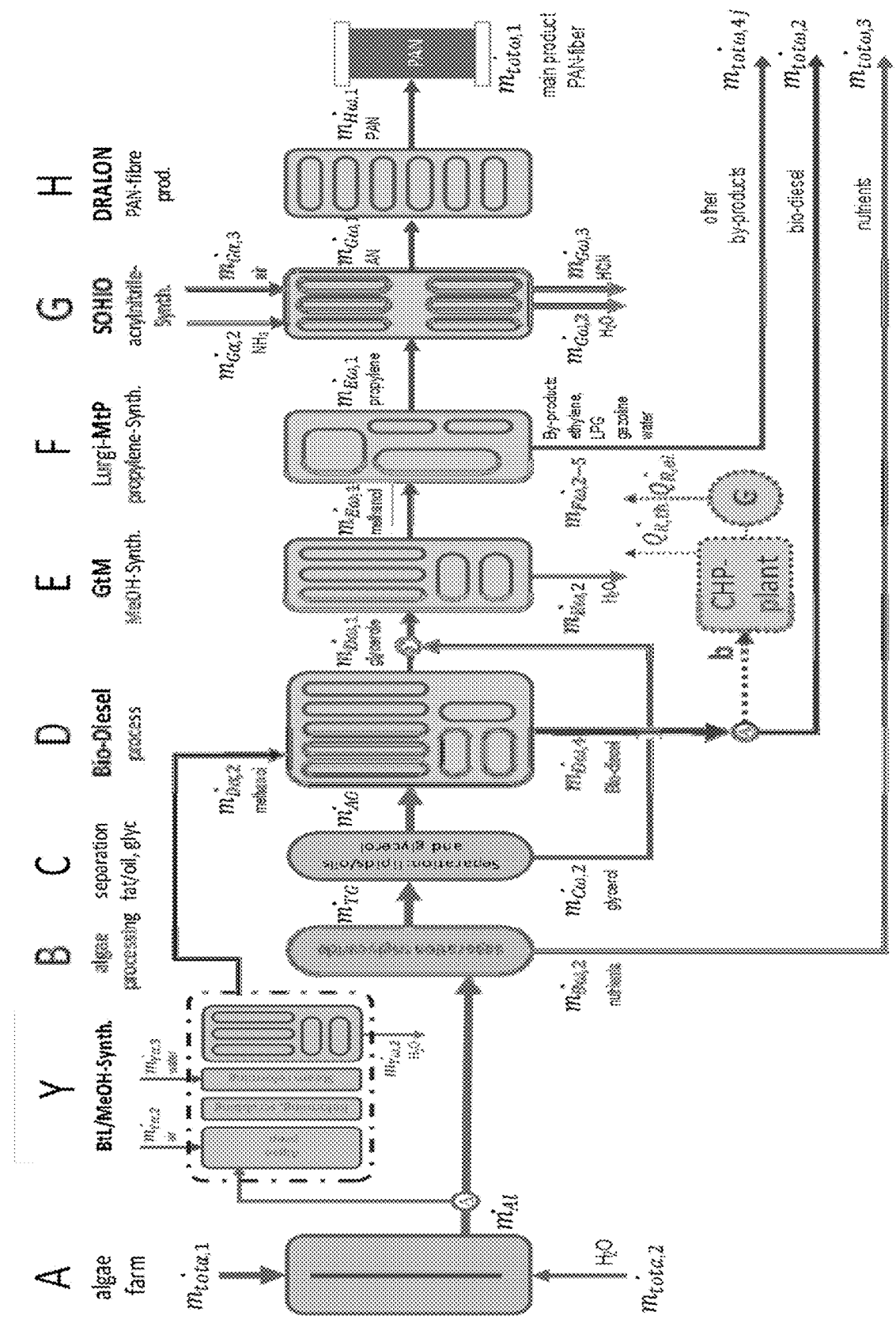
Figure 5:
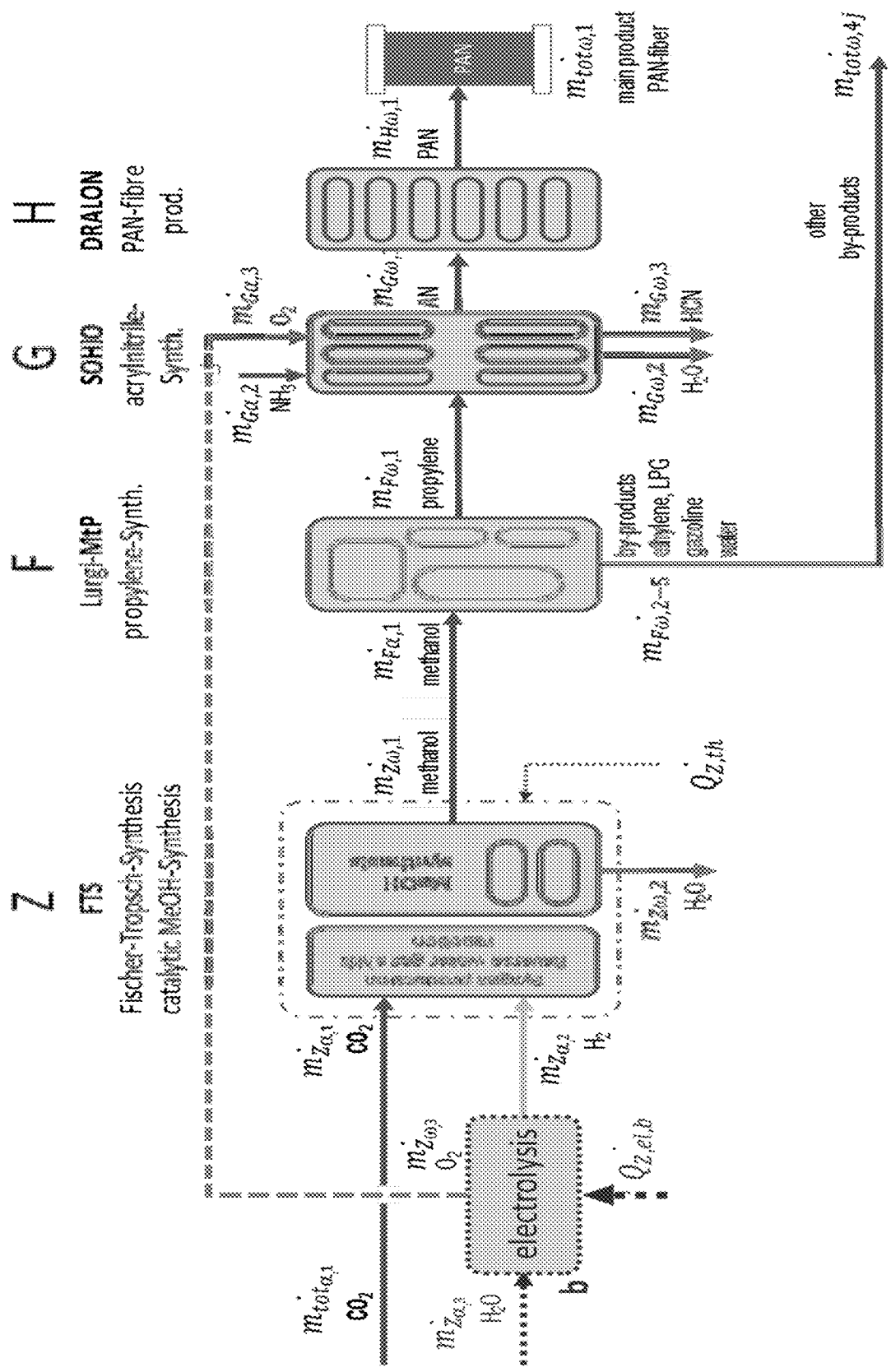
Figure 6:
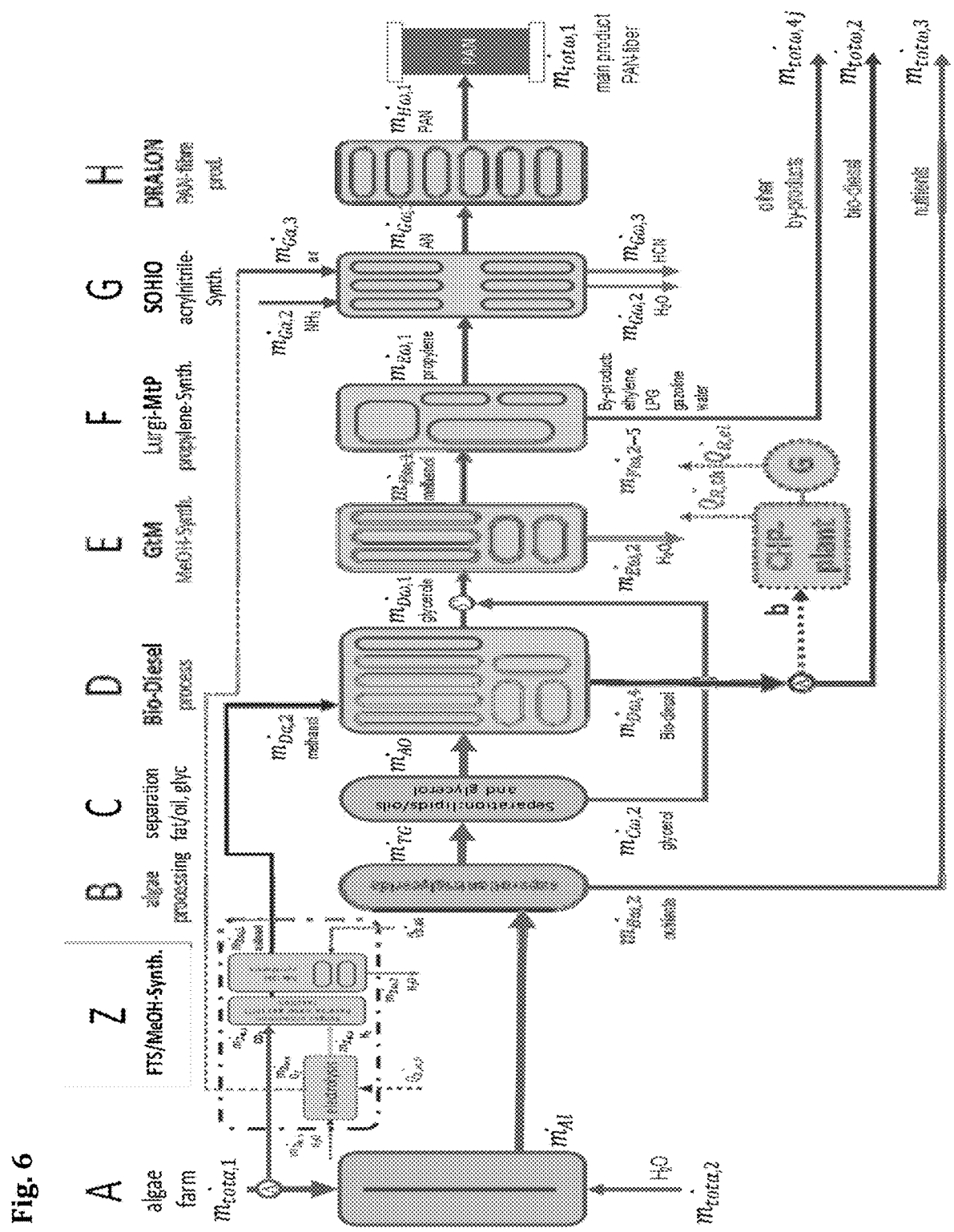
Figure 7:
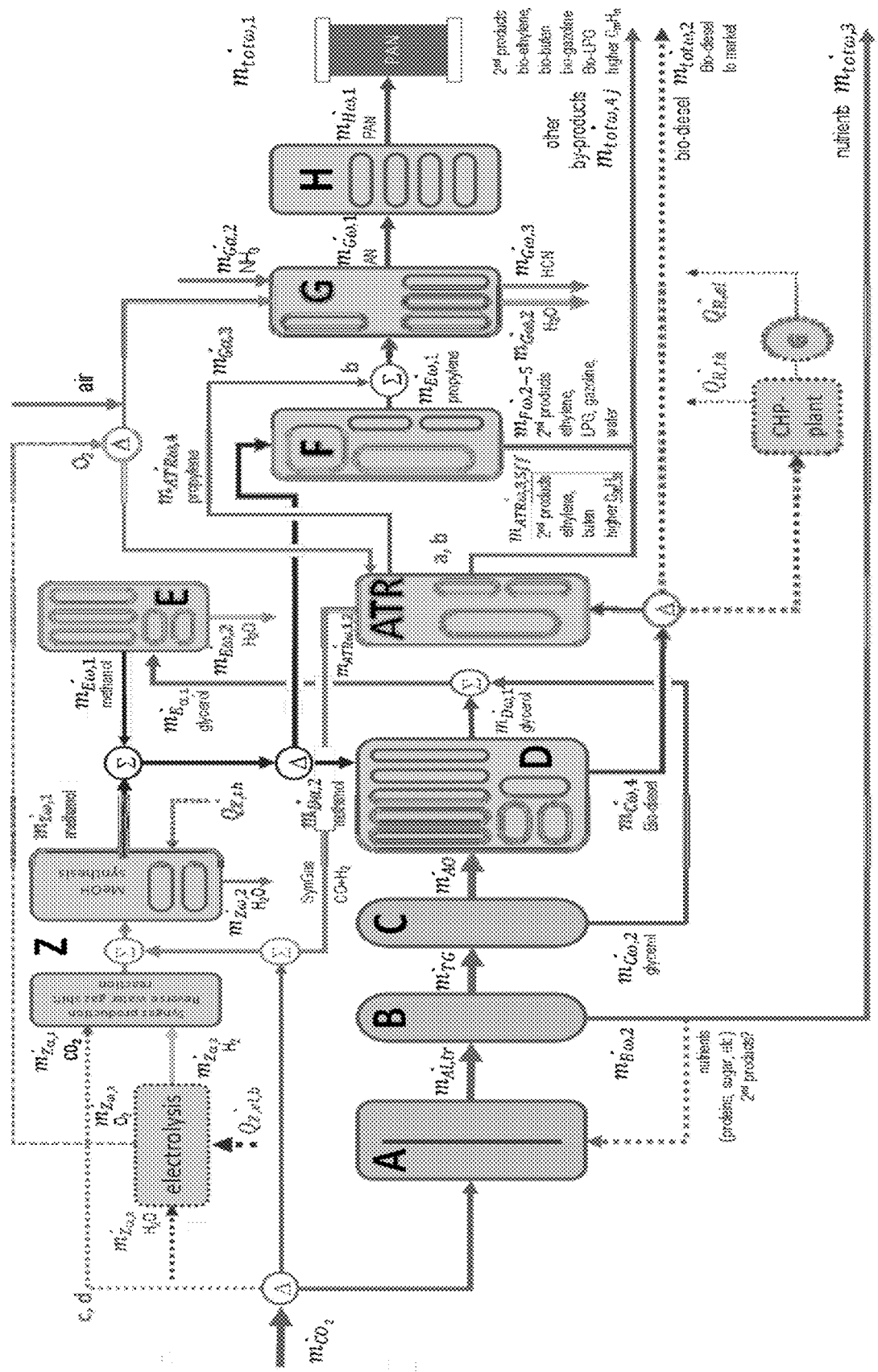
Figure 8:
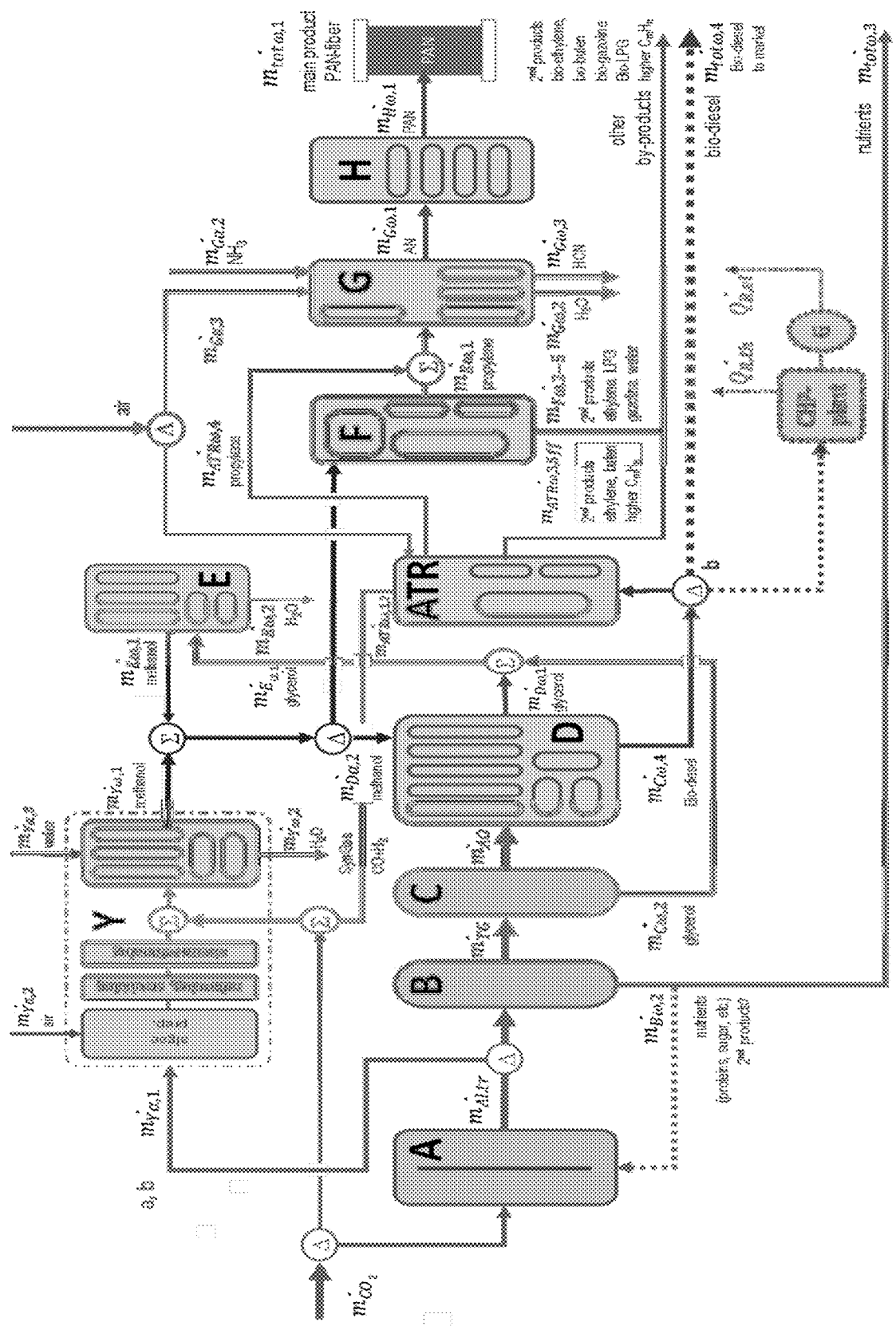

A   Algae farming
B   Algae processing 1: Separation of nutrients and triglycerides
C   Algae processing 2: splitting of triglycerides into glycerol and algae oil/lipids
D   Biodiesel-process: esterification of algae oil
E   GtM-process: conversion of glycerol into methanol
F   MtP-process (MOBIL-process): conversion of methanol into propylene
G   SOHIO-process: acrylonitrile synthesis on propylene basis
H   DRALON-process: alcrylonitrile polymerization to polyacrylonitrile fiber
X   GtAN-process (Fraunhofer): acrylonitrile synthesis on glycerol basis
Y   BtL/MeOH-process: algal biomass liquefaction and methanol synthesis
Z   FTS/MeOH-process: $CO_2$ reforming by Fischer Tropsch synthesis and methanol synthesis
ATR Autothermal reforming and partial oxidation of biodiesel
CHP CHP unit for combined heat and electricity generation by biodiesel incineration

CARBON FIBERS WHICH CAN BE PRODUCED REGENERATIVELY OR PART-REGENERATIVELY FROM CO2 USING COMBINED PRODUCTION METHODS

The Paris Agreement of December 2015 challenges the international community to keep the average global temperature increase below 2° C. by 2100 and beyond. For this purpose, measures are required which, (although) increasing the effort in process technology, significantly increase the efficiency of the conversion of CO2 into usable regeneratively produced material. The materials consists essentially of two categories of materials that drive the world economy. One category includes materials such as fuels, lubricating oils and other liquid or gaseous fuels for the operation of gas turbines, diesel power plants, the propulsion of aircraft, vehicles and ships, as well as the heating of buildings or the operation of cookers.

The second category involves the production of building and construction materials that can be produced from CO2.

The calculations of climate research show that there is a quasi-linear relationship between the concentration of CO2 in the atmosphere and global warming in terms of increasing the average Earth's atmosphere temperature. This scientific finding suggests that a further concentration of CO2 in the atmosphere must be prevented and, ideally, also reduced to preindustrial levels.

To achieve this, various measures are discussed. On the one hand, the introduction of renewable energy sources such as wind, water and solar power shall replace fossil fuels for energy production. The experience with the introduction of wind power and photovoltaic systems, for example in Germany, has led to the insight that these measures, while effective, are not sufficient to keep the global temperature of the earth under control. The state of the art describes methods by which fuels such as biodiesel or kerosene are obtained either via the production of biomass such as, for example, algae growth with sequestered or natural CO 2, or that these industry-relevant substances are recovered with the aid of the Fischer-Tropsch synthesis from sequestered CO2 and hydrogen. Both methods are technically possible, but have different efficiencies and associated costs. However, both methods also have different starting materials and different valuable by-products, in particular, for example, if the hydrogen obtained by electrolysis releases oxygen as a by-product.

Another goal of limiting global warming is the conversion of CO2 from fossil or natural sources into construction and building materials, as described in PCT/EP2009/008497. CO2 sequestration measures are therefore necessary at the beginning of such a new material production process chain, since the required CO2 from these sources is much cheaper to obtain or sequester than directly from the air, which has only a comparatively low CO2 concentration. An energy- and mass-efficient method for adsorption and binding of CO2 from atmospheric or sequestered sources is the production of algal biomass, which is about 20 times better than the equivalent CO2 binding with terrestrial plants due to the high growth rate of the organisms. The large-scale production of algae biomass is recommended for economic reasons in technically simple open cultivation basins, which are low-cost industrially scale. An alternative to the extraction of natural CO2 is the power generation, gasification or other energetic utilization of natural algae mass and in particular the sequestration of the CO2 from their flue gases. To bring the energy generation processes into regenerative status as soon as possible and to account for the fact that switching off fossil power generation systems is currently not possible without jeopardizing the world economy, but on the other hand stop CO2 emissions as quickly as possible as well, means that completely new processes have to be introduced which shift CO2 into a solid and stable aggregate state of carbon compounds as quickly as possible. Ideally, such a substance should be usable as a building material and construction material.

For this purpose, carbon fiber base material, so-called precursors are generated in a cost effective manner with reasonable space requirement from the CO2 through several different alternative paths or process chains, from which then with the help of carbonisation (through pyrolysis) tensile and especially very rigid carbon fibers are produced, which have a solid state of aggregation over millions of years. First, for example, carbon dioxide sequestered CO2 is introduced into algae tanks in addition to the amount of CO2 absorbed from the air to prevent it from entering the atmosphere. In the processes described here, for example, glycerol (glycerol) is obtained from the fats and oils of the algal biomass, with initially also a relatively large amount of biodiesel being produced as the basis for fuel such as kerosene or truck and ship fuel. This fuel can be burned at a later stage of the installation of plants in biodiesel power plants, either for power generation, whereby the sequestered CO2 is passed back into the algae tanks and is thus circulated, or for example by gasification to be supplied in whole or in part to the precursor production. The aim is to control the ratio of the production of valuable building materials for the industry as well as valuable fuel for the industry as needed. This need can be very different for example today compared to the future. In addition to the sequestered CO2, the algae cultivation tanks, which are preferably installed in sunny areas, absorb free CO2 from the ambient air when the air is preferably pumped directly to the algae tank water with the appropriate technology under high pressure and with the finest nozzles.

The novelty, however, is based on the knowledge that in addition to fuel, which can already be obtained from CO2, also basic chemicals such as polyacrylonitrile or other useful starting materials can be obtained from the processes described above, which are the starting materials for carbon fiber production. Although carbon fibers are already being traded as the material of the future, they have so far been little discussed in the light of the climate problem, because they are too energy-intensive in material production and therefore too low in mass to be climate-relevant. That will change with this invention. Although the production of carbon fibers from oil-containing algae biomass and their fats and oils has already been described to some extent, it has hitherto been unclear whether the necessary amounts of algal biomass on acceptable areas are even possible.

One of the possibilities is the production of acrylonitrile from the fats, fatty oils or oils of the algal biomass. Triglycerides, triglycerides, also glycerol triesters, more rarely obsolete referred to as neutral fats, are triple esters of the trivalent alcohol glycerol with three acid molecules and should according to the IUPAC recommendation exclusively referred to as triacylglycerols, short TAGs, (or exact tri-O-acylglycerole). The prefix Tri refers to three acyl acid residues esterified with glycerol.

Triacylglycerols with three fatty acids are the compounds in fats and fatty oils. Natural fats consist for the most part of triglycerols with three long-chain fatty acids, which usually consist of unbranched chains with 4 to 26, typically 12 to 22 carbon atoms. These are liquid at room temperature, and are also referred to as oils or, to distinguish them from mineral oils or essential oils, fatty oils. Pure triacylglycerols of fatty acids are also referred to as neutral fats. Suitable algae strains, including saltwater algae, are capable of producing large quantities of these fatty oils.

In addition, the question arises as to whether these processes can be represented in sunny regions alone in which little or no CO2 emissions are generated, as in the climatically rather cold industrial regions. With appropriate calculations, the realization has arisen that both the algal biomass production and its conversion into renewable chemical raw materials (such as biodiesel or biokerosin) with the by-product glycerol, as well as the Fischer-Tropsch-Synthesis via the detour of methanol production are able to produce acrylonitrile as a base material for the production of carbon fibers. The methanol is first converted into propene for this purpose, which then makes acrylonitrile and then polyacrylonitrile producible in the next step. The combination of these processes is described in this patent application as a means of promoting the production of carbon fibers from CO2 both in sunny countries currently experiencing little industry and in countries with little sunlight and high carbon footprint industries. Not all of these processes will have the same efficiency, but the transport routes and costs of material, that is, sequestered CO2 and building material, also play a significant role when looking at overall balance sheets. Therefore, the synthetic processes in this patent are accorded the same importance as the much more energy-efficient route over the algal biomass. Both processes have the same sociopolitical status in the fight against climate change in relation to the respective region; each region can use this invention to do the best possible in each situation.

Both methods have advantages and disadvantages. The advantage of algae synthesis is cost. Since in the production of glycerol accumulates a lot of biodiesel, which can be used for energy supply in the form of fuel, power generation and heating and due to its high value as a renewable energy carrier keeps the cost of glycerol production small and thus the cost of acrylonitrile, the method has the disadvantage that a relatively large area consumption is associated with this process.

The Fischer-Tropsch synthesis as the basis for the production of acrylonitrile from propene via the intermediate step methanol has not been described in the prior art and has in comparison to the production of algal biomass the advantage of a comparatively small area consumption, but also has the disadvantage of comparably higher costs, which can, however, be compensated by an initially correspondingly high CO2 emissions trading price. In the end, however, one would like to get along without emission rights in the long term and therefore reduce the production price.

This can be achieved by a combination of the processes, namely by a mixing ratio which, according to the necessary industrial transformation, can be adapted to these new processes. According to the calculations, a mixture ratio of 50 percent in each case appears long term as an optimal measure of this ratio, which can certainly be changed by optimizing technology to the one hand and the other, and is thus also a function of time. In the beginning, it makes sense to immediately process CO2 in industrial conurbations with the help of cheap wind power with Fischer-Tropsch instead of sending it on a long journey to North Africa. However, should algae efficiency increase over time in North Africa, then this sense of purpose may change in the future, the algae content can be driven up to lower the price of the polyacrylonitrile fiber on and on, at the same space consumption.

The electrolysis to produce the amounts of hydrogen required for the Fischer-Tropsch process releases quantities of oxygen needed for the process of producing acrylonitrile from the algal mass. This leads to an increase in the overall efficiency and thus to a reduction in the price of the polyacrylonitrile fibers. The combination of the methods yields further advantages as a by-product.

One of the major benefits of the combination of algae-based carbon fiber production and Fischer-Tropsch processes described herein, which is initially available for carbon fiber production to industries in the already industrialized world, is a gradual, gentle transfer of technology to the sun-rich and therefore, as a rule, poorer countries and the relocation of processes to those regions which today are still economically disadvantaged, while climate negotiations are increasingly being determined by the gradual adjustment of the current unbalanced North-South decline.

The following processes form the building blocks for the new process chains claimed in the claims of the application in order to produce polyacrylonitrile from CO2 via algal biomass for the production of bio-carbon fibers. 8 process chains are described below, as illustrated in FIGS. 1. to 8. and the sequence of the processes with the associated mass flows is described as follows:

1. 1st Process Chain 1, Algae→Biodiesel Process→GtM-→MOBIL (MtP)→SOHIO→DRALON
   a) without MeOH cycle and without energetic use of biodiesel
   b) without MeOH cycle, with energetic biodiesel use
   c) with MeOH cycle and without energetic use of biodiesel
   d) with MeOH cycle and with energetic biodiesel use
2. Process chain 2, algae→Biodiesel process→GtAN-→DRALON
   a) without energetic biodiesel use
   b) with energetic biodiesel use
3. Process Chain 3, Algae→BtL/MeOH Synthesis Process→MOBIL (MtP)→SOHIO→DRALON
4. Process chain 4, like 1 but with upstream MeOH production via BtL/MeOH synthesis
   a) without energetic biodiesel use
   b) with energetic biodiesel use
5. Process chain 5, CO2→FTS+MeOH synthesis→MOBIL (MtP)→SOHIO→DRALON
   a) without upstream electrolysis for H2 supply
   b) with upstream electrolysis for H2 supply
6. Process chain 6, like 1 but with upstream MeOH production via FTS/MeOH synthesis
   a) without energetic biodiesel use
   b) with energetic biodiesel use
7. Process chain 7, like 6 but with autothermal reforming (ATR) of biodiesel with partial biodiesel oxidation and FTS/MeOH synthesis
   a) high-temperature ATR, air supply, max. syngas
   b) low-temperature ATR, exclusion of air, max. propylene
   c) as a) but with +9% CO2 feed towards FTS
   d) like a) but with +50% CO2 feed towards FTS
8. Process chain 8, like 7a but with upstream BtL/MeOH synth. for syngas use
   a) 60% of the total biomass supply towards BtL
   b) 90% of the total biomass supply towards BtL
9. The legend for the processes described above with regard to the labeling in the figures is shown in FIG. 9:
   A algae Growth in salt water, production of algae biomass from CO2
   B algae process 1: separating into nutrients and triglycerides C algae Process 2: Splitting the triglycerides into glycerol and light algae oils and lipids
D Biodiesel process: esterification of algae oil
E GtM-Process: Conversion of glycerol into methanol
F MtP-process (MOBIL-Process): Conversion of methanol into propylene (propene)
G SOHIO Process: Acrylonitrile Synthesis from Propylene
H DRALON-process: Alcrylonitrile Polymerization to polyacrylonitrile fibers (spinning solution in the spinning bath becomes PAN fibers)
X GtAN-Process (Fraunhofer patent): direct acrylonitrile synthesis from glycerol
Y BtL/MeOH process: liquefaction of algal biomass and methanol synthesis
Z FTS/MeOH process: $CO_2$ cleavage by Fischer-Tropsch synthesis and methanol synthesis
ATR autothermal reforming and partial oxidation of biodiesel
CHP CHP Unit for Combined Heat and Electricity Generation through Biodiesel Combustion The process chains outlined in the accompanying drawings 1-9 and thus clearly described, are the basis of the production of bio-carbon fiber based on polyacrylonitrile (PAN), form the fundament for the following patent claims.

What is claimed is:

1. A process of producing polyacrylonitrile-based carbon fibers comprising a combination of two or more of the following steps:
   a) producing algae biomass by utilizing sequestered or natural $CO_2$;
      separating polyacrylonitrile triglycerides from said algae biomass;
      splitting said triglycerides into glycerol and algae oil/lipids;
      converting said glycerol into methanol using a glycerol to methanol process;
      converting said methanol into propylene via a methanol to propylene process;
      producing acrylonitrile from said propylene via an acrylonitrile-synthesis process; and,
      obtaining polyacrylonitrile from said acrylonitrile via a polyacrylonitrile-fiber production process;
   b) producing biomass by utilizing sequestered or natural $CO_2$; liquefaction of said biomass and methanol synthesis via a biomass to liquid process with conversion into methanol;
      converting said methanol produced from step "b)" into propylene via a methanol to propylene process;
      producing acrylonitrile from said propylene via an acrylonitrile-synthesis process; and,
      obtaining polyacrylonitrile from said acrylonitrile via a polyacrylonitrile-fiber production process;
   c) producing biomass by utilizing sequestered or natural $CO_2$;
      separating triglycerides from said biomass;
      splitting said triglycerides into glycerol and oil/lipids;
      converting said glycerol into methanol using a glycerol to methanol process as a first source of methanol;
      converting said oil/lipids into methanol as a second source of methanol through esterification of said oil/lipids and an auto-thermal reforming process of the esterification product into synthesis gas and its conversion via methanol synthesis into methanol;
      converting the methanol from both the first source and the second source into propylene via a methanol to propylene process;
      producing acrylonitrile from said propylene via an acrylonitrile-synthesis process; and,
      obtaining polyacrylonitrile from said acrylonitrile via a polyacrylonitrile-fiber production process;
   d) producing methanol from $CO_2$ reforming by a reverse water-gas shift reaction and a Fischer-Tropsch synthesis utilizing $H_2$, by conversion of $CO_2$ and $H_2$ into methanol;
      converting said methanol produced from step "d)" into propene or propylene via a methanol to propylene process;
      producing acrylonitrile from said propene via an acrylonitrile-synthesis process; and,
      obtaining polyacrylonitrile from said acrylonitrile via a polyacrylonitrile-fiber production process,
   said processes a), b), c) and d) further comprising:
   e) obtaining the $CO_2$ required for the polyacrylonitrile-fiber production process from at least one of: (i) flue gases from fossil power plants, (ii) process-related $CO_2$ emissions from production of steel, cement or aluminum, (iii) natural sources;
   f) obtaining the $CO_2$ required for the polyacrylonitrile-fiber production process from flue gases of regenerative biodiesel power plants;
   g) obtaining the $CO_2$ required for the polyacrylonitrile-fiber production process from flue gases of natural biomass that has previously been generating electricity;
   h) obtaining the $CO_2$ for the algae oil production from ambient air.

2. The process of claim 1, further comprising obtaining oxygen required for the polyacrylonitrile-fiber production process from an electrolysis process of hydrogen production used in the process of producing methanol from $CO_2$ reforming by the Fischer-Tropsch synthesis.

3. The process of claim 1, further comprising obtaining electricity required for the polyacrylonitrile-fiber production from a biomass-electricity conversion or other regenerative electricity.

4. The process of claim 1, further comprising obtaining $CO_2$ from ambient air being pumped under high pressure through designated nozzles directly to said algae cultivation basins.

* * * * *